US012293835B1

United States Patent
Mathur et al.

(10) Patent No.: US 12,293,835 B1
(45) Date of Patent: May 6, 2025

(54) SYSTEMS AND METHODS FOR AUTHORIZATION AUTOMATION USING ARTIFICIAL INTELLIGENCE

(71) Applicant: Elevance Health, Inc., Indianapolis, IN (US)

(72) Inventors: Ayush Mathur, Novi, MI (US); Brian Fornelli, Indianapolis, IN (US); Xiaoyu Sun, Indianapolis, IN (US); Xinkai Chen, Indianapolis, IN (US); James D. Martindale, Indianapolis, IN (US); Harsha Arcot, Indianapolis, IN (US); Madeline Glasheen, Indianapolis, IN (US); Summer Ashley, Indianapolis, IN (US); Stephanie Wilson-English, Indianapolis, IN (US); Anthony Nguyen, Indianapolis, IN (US); Vincent Pantone, Indianapolis, IN (US); Urmesh Shah, Indianapolis, IN (US); Chao Zhang, Indianapolis, IN (US); Pice Chen, Indianapolis, IN (US); Adarsh Ramesh, Schaumburg, CT (US)

(73) Assignee: Elevance Health, Inc., Indianapolis, IN (US)

( * ) Notice: Subject to any disclaimer, the term of this patent is extended or adjusted under 35 U.S.C. 154(b) by 125 days.

(21) Appl. No.: 18/300,249

(22) Filed: Apr. 13, 2023

Related U.S. Application Data (60) Provisional application No. 63/362,918, filed on Apr. 13, 2022.

(51) Int. Cl.
   *G16H 50/20* (2018.01)
(52) U.S. Cl.
   CPC .................................. *G16H 50/20* (2018.01)

(58) Field of Classification Search
   CPC ...................................................... G16H 50/20
   See application file for complete search history.

(56) References Cited

U.S. PATENT DOCUMENTS

| 9,230,061 B2 | 1/2016 | Ephrat et al. |
| 2019/0034503 A1 | 1/2019 | Ephrat et al. |
| 2024/0153639 A1* | 5/2024 | Elidan ..................... G16H 50/70 |

FOREIGN PATENT DOCUMENTS

WO WO-2017059022 A1 * 4/2017 ............. G06N 20/20

OTHER PUBLICATIONS

Pomares-Quimbaya et. al. "A Strategy for Prioritizing Electronic Medical Records Using Structured Analysis and Natural Language Processing." Revista Ingenieria y Universidad 22.1: 7(25). Pontificia Universidad Javeriana. (Jan. 2018-Jun. 2018) (Year: 2018).*

(Continued)

*Primary Examiner* — Linh Giang Le
(74) *Attorney, Agent, or Firm* — Morgan, Lewis & Bockius LLP (57) ABSTRACT

An improved machine learning based method for authorizing the performance of a treatment, comprising the steps of: receiving a treatment authorization request, the treatment authorization request including a historical record of the person who will receive the treatment and treatment identifying information relating to the treatment; creating an extracted text of the historical record using optical character recognition on the historical record; determining whether to analyze authorization performance of the treatment using a machine learning authorization process, wherein the determination is based on treatment identifying information and whether treatment authorization guidelines exist for the identified treatment; in response to a determination to analyze authorization performance of the treatment using a machine learning authorization process: identifying authorization criteria for the treatment based on the treatment (Continued)

authorization guidelines, wherein the authorization criteria includes records data conditional to authorization of performance of the treatment; identifying a natural language record processing model corresponding to the expense authorization guidelines; and performing natural language processing on the extracted text of the record in accordance with the identified natural language record processing model to identify relevant record data in the record; determining whether the relevant record data meets the authorization criteria and in response to a determination that the relevant record data meets the authorization criteria, authorizing the performance of the treatment.

9 Claims, 4 Drawing Sheets

(56) References Cited

OTHER PUBLICATIONS https://www.changehealthcare.com/clinical-decision-support/interqual-autoreview.

* cited by examiner

SmartPASS: NLP Rule-Based Findings

250

260
DCN: RCAP20210328003991
AUTH ID: 16000003
Case Approved

| | | Where was this found in the medical record? |
|---|---|---|
| 1. Gastroparesis 210 | {"history of present illness": "female with idiopathic gastroparesis."} | Page 3, Paragraph 6 |
| 2. Intolerance/Contraindicated to Medications 212 | {"encounter status": "She has been tried on the antiemetic agents, Compazine and Zofran, which also did not help her symptoms."} | Page 20, Paragraph 1 |
| 3. Refractory/Medical Therapy 214 | {"encounter status": "Enterra Therapy is indicated for the treatment of chronic intractable (drug-refractory) nausea and vomiting secondary to gastroparesis of diabetic or idiopathic etiology."} | Page 19, Paragraph 1 |
| 4. Gastric Empty Test 216 | {"encounter status": "Her present symptoms consist of severe nausea and vomiting that is related to delayed gastric emptying."} | Page 22, Paragraph 1 |

SYSTEMS AND METHODS FOR AUTHORIZATION AUTOMATION USING ARTIFICIAL INTELLIGENCE

CROSS-REFERENCE TO RELATED APPLICATIONS

This application claims the benefit of U.S. Provisional Application No. 63/362,918, filed Apr. 13, 2022, the entirety of which is incorporated herein by reference.

TECHNICAL FIELD

The disclosed implementations relate generally to automated expense approval systems using natural language processing, and more specifically to systems and methods for clinical decision automation in a health care setting.

BACKGROUND

As healthcare costs continue to increase at historical rates, health insurers play a key role in ensuring that healthcare costs remain in control for their respective customers and healthcare providers. One of the most popular and prevalent channels for health plans in controlling healthcare costs is by defining, implementing, and continuously improving robust utilization management (UM) processes and functions. Utilization management at its core is ensuring the care that a patient is expected to receive is medically necessary given industry and health plan accepted criteria and that the care is appropriate given the unique condition and history of the patient, before agreeing to cover it. These UM processes are presented to patients and providers using terminology such as prior-authorizations, pre-certifications, referrals, and appeals.

Internally within health payors, UM processes are rooted in the delivery of a decision of whether or not the requested health service, equipment, or care for the specific patient is approved based on the aforementioned medical necessity criteria. This utilization review is typically done by clinical practitioners who manually review the clinical documentation received in support of the request, which may include the patient's relevant medical records, and the medical necessity criteria, which may be defined by industry or health insurer standards, to make the ultimate decision on coverage. The parallel review of clinical documentation and medical necessity criteria is a manual, labor intensive, and demanding task as subjective clinical evidence must be found and documented to support every respective medical necessity criteria present in the standards leveraged.

It would be advantageous to automate this process, by having a system to apply the medical necessity criteria to the medical records, by analyzing the text of the medical records to determine whether the medical necessity criteria are met by what is disclosed in the medical records. Historical challenges in delivering automation associated to this invention stem from the following challenges within clinical settings and applications: low quality outputs from optical character recognition (OCR), lack of maturity from the natural language processing (NLP) artificial intelligence (AI) models, and a lack of integration within appropriate business/clinical workflows and systems. These challenges were intensified given the complex, clinical nature of the source documentation in question-medical records that are rich in complex and non-standardized terms as used by individual medical practitioners, clinical shorthand, rich data, and written artifacts. The medical necessity criteria are also complex in their own right, driven by complex medical jargon that does not easily lend itself to machine analysis or repetitive matching. Due to enhancements of OCR and NLP/AI more recently, designing, building, and implementing a system that meaningfully addresses the challenges in scope can now be achieved as evidenced by the present disclosure.

SUMMARY

Accordingly, there is a need for systems and methods to drive automation in the approval of expenses, including insurance claims, the approval of which depends on the contents of clinical documentation. By automating the testing of the clinical documentations for evidence of medical necessity criteria, and in some embodiments by automating the training of the system to identify the clinical criteria themselves, the method described herein, in some implementations, uses trained models to improve the time required to automate approvals and the accuracy of the approval result. Benefits include increased provider and member satisfaction with the utilization management process, increased administrative bandwidth to focus on more member centric programs and increased turn-around-time (TAT) results reported to regulatory bodies and customers.

In another aspect, a system configured to perform any of the above methods is provided, according to some implementations.

In one embodiment, an improved machine learning based method for authorizing the performance of a treatment is disclosed. The method comprises the steps of receiving a treatment authorization request, the treatment authorization request including a historical record of the person who will receive the treatment and treatment identifying information relating to the treatment, creating an extracted text of the historical record using optical character recognition on the historical record, and determining whether to analyze authorization performance of the treatment using a machine learning authorization process, wherein the determination is based on treatment identifying information and whether treatment authorization guidelines exist for the identified treatment. In response to a determination to analyze authorization performance of the treatment using a machine learning authorization process, the method further comprises the steps of identifying authorization criteria for the treatment based on the treatment authorization guidelines, wherein the authorization criteria includes records data conditional to authorization of performance of the treatment, identifying a natural language record processing model corresponding to the treatment authorization guidelines, performing natural language processing on the extracted text of the record in accordance with the identified natural language record processing model to identify relevant record data in the record, determining whether the relevant record data meets the authorization criteria, and in response to a determination that the relevant record data meets the authorization criteria, authorizing the treatment.

In some embodiments the method also comprises the step of cropping and deskewing each page of the clinical documentation prior to the step of creating the extracted text. In some embodiments, the authorization criteria comprise a plurality of necessity concept groups, wherein each of the plurality of necessity concept groups comprises a plurality of words of phrases corresponding to one authorization criterion. In some embodiments, the method further comprises the steps of creating a decision tree comprising Boolean logical operators to the plurality of necessity concept groups to create at least one subset of necessity concept groups that are required to be found in the historical record and traversing the decision tree to determine whether the relevant record data meets the authorization criteria.

In some embodiments, the treatment is a medical treatment and the historical record is a medical record. In some embodiments, the treatment authorization guidelines relate to the medical necessity of the medical treatment.

In some embodiments, the method further comprises the step of, in response to a determination that the relevant record data does not meet the authorization criteria, analyzing the extracted text to generate a classification label for each page of the medical record, using a multinomial classifier model comprising a long short-term memory (LSTM) neural network, wherein the multinomial classifier model has been trained to recognize different classes of page, based on similarities to a corpus of historical pages that have been previously classified, recognizing a specified keyword within the extracted text, using a named entity recognition model (NER), wherein the NER is trained using policy data relating to a policy having the policy type, and wherein the specified keyword is identified as relating to the policy type, and displaying a visual representation of the clinical document on a display, wherein the visual representation comprises a visual indicator of the presence of the specified keyword on the page, and a visual indicator of the classification label.

A system comprising one or more memory units each operable to store at least one program and at least one processor communicatively coupled to the one or more memory units, in which the at least one program, when executed by the at least one processor, causes the at least one processor to perform the operations of the method discussed above, is also disclosed.

A non-transitory computer readable storage medium having stored thereon computer-executable instructions which, when executed by a processor, perform the steps of the method, is also disclosed.

BRIEF DESCRIPTION OF THE DRAWINGS

For a better understanding of the various described implementations, reference should be made to the Description of Implementations below, in conjunction with the following drawings in which like reference numerals refer to corresponding parts throughout the figures.

DESCRIPTION OF IMPLEMENTATIONS

Reference will now be made in detail to implementations, examples of which are illustrated in the accompanying drawings. In the following detailed description, numerous specific details are set forth in order to provide a thorough understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

It will also be understood that, although the terms first, second, etc. are, in some instances, used herein to describe various elements, these elements should not be limited by these terms. These terms are only used to distinguish one element from another. For example, a first electronic device could be termed a second electronic device, and, similarly, a second electronic device could be termed a first electronic device, without departing from the scope of the various described implementations. The first electronic device and the second electronic device are both electronic devices, but they are not necessarily the same electronic device.

The terminology used in the description of the various described implementations herein is for the purpose of describing particular implementations only and is not intended to be limiting. As used in the description of the various described implementations and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" is, optionally, construed to mean "when" or "upon" or "in response to determining" or "in response to detecting" or "in accordance with a determination that," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]" or "in accordance with a determination that [a stated condition or event] is detected," depending on the context.

The system and method of the present disclosure is intended to automate the matching of clinical evidence received to a set of defined criteria or requirements set forth in an industry or company endorsed policy or guideline, e.g. relating to a medical procedure or other treatment, in order to drive an adjudication decision on an whether the expense related to the procedure or treatment is authorized. This deterministic system is intended to consume clinical documentation (e.g. faxes, notes, electronic medical records (EMR), etc.) and leverage codified clinical requirements to identify where within the clinical documentation there exist clinical evidence to meet the requirements stated in the policy or guideline, if at all. If the system does not find all needed clinical evidence to meet all requirements, an output is provided to a clinician to drive efficiencies in their manual review and adjudication.

Historically in the medical insurance industry, more than 80% of prior-authorization requests are approved. Medical providers are often dissatisfied with the length of time it takes to receive a decision response to their requests for prior authorization to perform their services and treatments. Furthermore, high administrative expenses are utilized to perform these reviews when they are manually performed by clinical staff. By automating identification of medical necessity criteria found in received medical records, the system of the present disclosure will be able to automate approvals for those where all required medical necessity criteria information is found, and, where all required medical necessity criteria are not found, the system will be able to share this information with clinicians to hasten the review process. In one aspect, the system may also share the records with clinicians in an enhanced way, so that relevant medical terms are easier to locate within the medical records. Benefits of automation include increased provider and member satisfaction with the utilization management process, increased administrative bandwidth to focus on more member centric programs, and faster turnaround time (TAT) results reported to regulatory bodies and customers.

Figure 1:
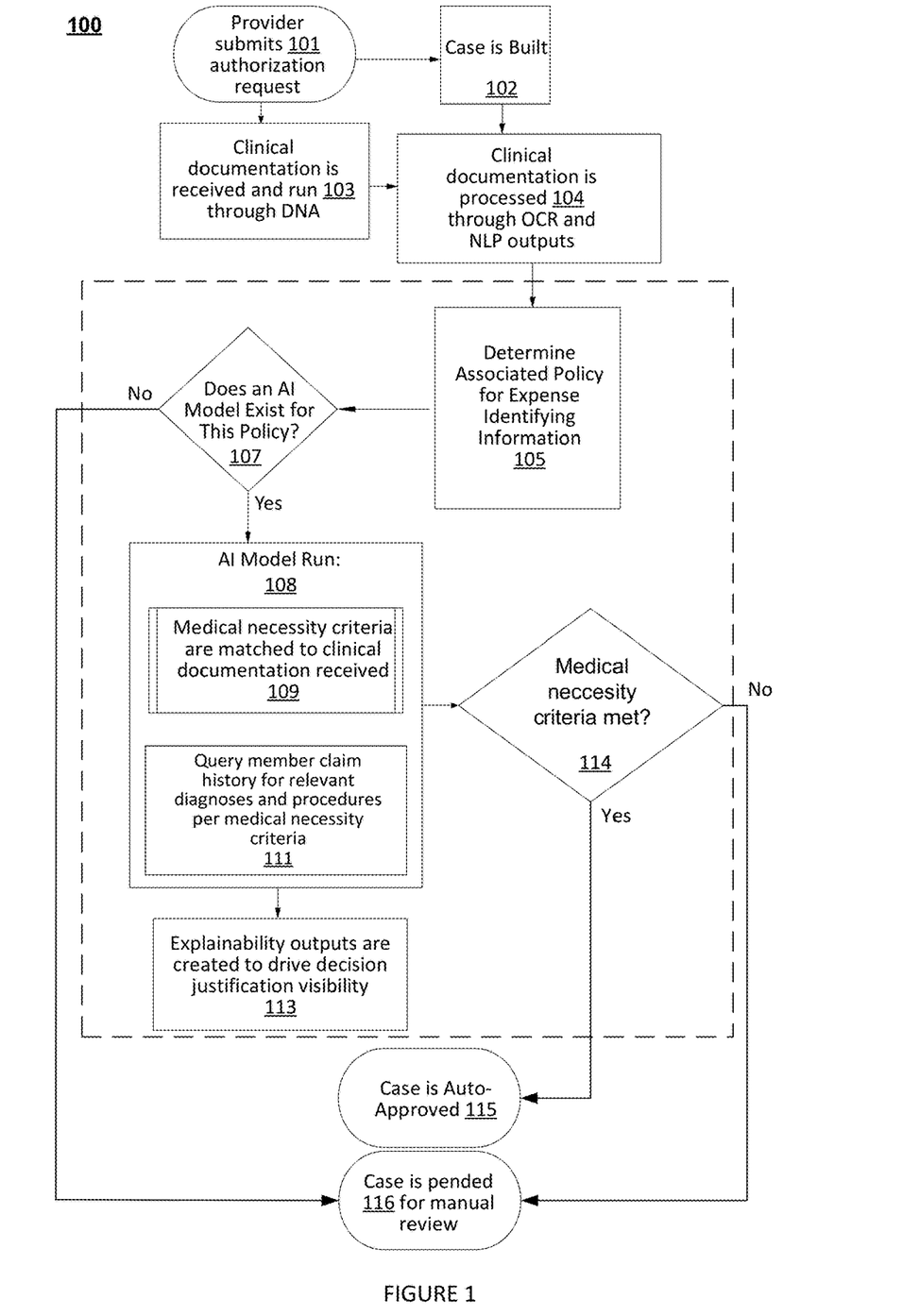
FIG. 1 is a flowchart of a method for automating clinical authorization, according to some implementations.

FIG. 1 is a flow chart illustrating a natural language processing method to automate the identification of medically necessary information, according to some implementations.

The method includes the provider submitting 101 an authorization request (also referred to herein as a procedure authorization request) for a medical procedure or other treatment. As used herein, "treatment" refers to any type of medical care, including procedures, drugs, tests, or other treatments or diagnostics. In some embodiments, the provider may be any medical practitioner interacting with clinical data (e.g., physician, nurse practitioner, etc.). The authorization request can be received through an Electronic Medical Records (EMR) interface, fax, email, upload, or any other means of transferring data. Upon receiving an authorization request, a first case is built. In some embodiments, every time an authorization request is received, a new case may be associated (102) with it. In other embodiments, every time an authorization request is received, the authorization request may be linked to an existing case (e.g., a case that was previously pending, denied, etc.) Each individual case may include all necessary data for the specific patient with whom the case is associated, such as a historical record of the patient. The historical record of the patient may include all prior diagnosis, procedures and medications for the patient, which may be in the form of data about prior insurance claims. In some embodiments, a case may be built on validations which may include member benefits, eligibility of service, pre-certification requirements, pre-determination requirements, servicing provider is in-network and/or facility is in-network.

After determining the provider is eligible, the method 100 includes receiving (103) clinical documentation from the provider for the clinical case. In some embodiments, received documents may be pre-processed by a document processing system that may be known as a Digital Nursing Assistant ("DNA"), which may pre-process the documents. The DNA system may be as described in U.S. patent application Ser. No. 18/168,408, which is incorporated herein by reference in its entirety.

The system may generate extracted text from the processed page using OCR, analyze the extracted text to generate a classification label for the page using a multinomial classifier model. The multinomial classifier model may in some embodiments comprise a long short-term memory (LSTM) neural network. The multinomial classifier model may be trained to recognize different classes of page, based on similarities to a corpus of historical pages that have been previously classified. Specified keywords may be recognized within the extracted text, which may occur using a named entity recognition model (NER). The NER may be trained using policy data relating to a policy having the policy type. The specified keyword may be identified as relating to the policy type.

The clinical documentation may include one or more medical records. In some embodiments, the provider receives a notification that they are eligible to submit their request. In some embodiments, after determining eligibility for the provider, the method 100 includes processing (104) the received clinical documentation using optical character recognition (OCR) and natural language processing (NLP) resulting in extracted text from the clinical documentation. Because clinical documentation frequently includes documents that were faxed, scanned, photocopied, or otherwise reproduced in such a way that artifacts are added or the image is degraded, the method 100 may in some embodiments include processing the clinical documentation includes cropping and deskewing each page of the clinical documentation. Doing so removes fax transmission headers and footers, detects page orientation, and corrects skewed images resulting from scanning the record. This improves the optical character recognition (OCR) process as discussed below. In some embodiments, OCR includes applying an OCR library of medical specific terminology and then using the OCR library to extract text from each page of the clinical documentation along with coordinates of the text and confidence scores for the recognized text. In some embodiments, the metadata on confidence allows filtering out low-confidence results, and the metadata on the coordinates of the text within the page allows providing highlighting capabilities in the system.

The method 100 includes identifying (105) an associated policy based on treatment identifying information, which may in some embodiments be a part of the clinical data or may in some embodiments be received along with the clinical data, e.g. specifically chosen by the provider who is initiating the treatment request. Treatment identifying information may include (i) a billed procedure code and/or a diagnosis code. An example of a billed procedure code may include: "31252: nasal/sinus endoscopy, surgical with ethmoidectomy; total (anterior and posterior) including frontal sinus exploration, with removal of tissue from frontal sinus, when performed." An example of a diagnosis code may include: "31287: nasal, sinus endoscopy, surgical with sphenoidotomy." In some embodiments, the system of the present disclosure may identify the treatment using the diagnosis code. In this example, the treatment model from the diagnosis code may be functional endoscopic sinus surgery model (CG-SURG-24).

Returning to FIG. 1, the method 100 includes determining (107) if a trained artificial intelligence (AI) model exists for the matching policy. A trained AI model may also be referred to as a set of procedure authorization guidelines. If a determination (107) is made that a trained AI model does not exist, the case is pended (116) for manual review. In some embodiments, manual review may include a medical practitioner reviewing the case. In some embodiments, the manual review of the clinical documents may be aided by the Digital Nursing Assistant system for processing the medical records to highlight relevant policy-specific terms, as discussed above and described in U.S. patent application Ser. No. 18/168,408.

Upon determining that a trained AI model exists for the matching policy, the method 100 includes running (108) the trained AI model on the extracted text. The trained AI model may in some embodiments be a policy-specific medical necessity rules based model that may have been built and/or trained based on translating authorization criteria, including records data relating to medical necessity that are conditional to the authorization, into discrete necessity concept groups, which may be referred to as "clinical cards," as discussed in further detail below. The AI model may be trained on the separate clinical cards, which may include expanding each clinical card based on modifiers and synonyms. Necessity concept groups may represent atomic concepts for clinical requirements. These concepts may include, what symptoms the patient must present, for how long the patient may have had the symptoms, what the diagnosis must be, what other treatments must have been tried previously before this treatment is authorized, or what tests are required to have been performed. Other concepts of medical necessity categories may also be used.

For example, as will be explained in relation to FIGS. 2A and 2B, four clinical cards 210, 212, 214 and 216 are illustrated, and all refer to different medical criteria that may be considered when evaluating whether to cover a gastric procedure. In one example, FIG. 2B illustrates gastroparesis, contraindication for prokinetic, contraindication for antiemetic and gastric emptying. Each clinical card has a built-in interpretation regarding how authorization would be approved. In the context of this example, for CG-SURG-70, there were four (4) clinical cards created, each with their own synonyms and modifiers that would lead to an interpretation in terms of eligibility for approval if the terms or their synonyms appeared in a submitted medical record. Clinical cards may be codified by at least one of synonyms and modifiers and may also be expanded based on clinical expertise and input (which may include, in this example, a list of brand and generic names for relevant drugs).

If a trained AI model does exist for the identified policy, an authorization process is run (108) using the AI model, on the extracted text. In some embodiments, the authorization process is a machine learning authorization process. Running (108) the AI model may include mining the clinical documentation for evidence of the necessity concept groups, e.g. the clinical cards, using a natural language records processing model. For example, the AI model may analyze the extracted text to determine whether the key phrases, of which it has been made aware, which may include modifiers or synonyms, are present in the medical record. The trained AI model is created using clinical input in translating the medical necessity criteria of a specific clinical model (e.g., guideline policy) into machine-understandable statements that can be mined for in the medical record in the management portal. In one embodiment, the list of key phrases is manually created, e.g. by clinical staff, and then stored in a storage medium, wherein it is associated with the relevant policy. The extracted text may then be evaluated to see whether the key phrases, or synonyms or modifiers of the key phrases, are present in the extracted text. In another embodiment, a manually collected list of key phrases may act as a training corpus for a natural language processing AI model, which is able to expand its analytical capabilities by evaluating the phrases in the context of the remainder of the medical record, in order to render a more accurate result that that aspect of clinical necessity is met. In another embodiment, machine learning may be used to further process the list of key phrases so that other similar key phrases that may be found may also be flagged as evidence of medical necessity. In another embodiment, machine learning may be used to directly search the medical record to extract semantically similar sentences and phrases to the clinical necessity criteria. This embodiment relies on pretrained language models which are fine-tuned on corpora such as the annotated i2b2 clinical corpus to embed words and sentences into a high-dimensional vector space. This embedding allows for an automated quantification of semantic similarity between the extracted medical record sentence or phrase and a given clinical necessity criterion.

The AI model is then run as to each of the necessity concept groups, to determine (109) whether the medical record contains evidence of the associated necessity concept. In one embodiment, member claim history may also be queried (111) for evidence of each necessity concept group. For some policies, different subsets of necessity concept groups may be required for approval, e.g. there may be alternative medical reasons why the same procedure might be approved for different patients or medical circumstances. Accordingly, the analysis may also include layering a decision tree over evidence of the clinical cards, reflecting the clinical interpretation in regards to approval of the authorization request. For example, as shown in FIG. 2A, for Gastric Electric Stimulation, positive evidence of all four of cards 210, 212, 214 and 216 may be required. For other policies or treatment types, medical necessity may be proven if only card 210 OR card 212 were met, along with card 214 AND card 216. As such, logic for approval may require "(210 OR 212) AND 214 AND 216." The approval logic varies by policy, but can be represented by a decision tree. This representation allows for instant interpretability of the model outputs in relation to clinical concepts.

The trained AI model entails a rules-based system for matching (109) clinical necessity criteria from the guideline to specific sentences within the medical record. The trained AI model mimics clinician decision making process by determining if clinical documentation has appropriate evidence of matching respective clinical criteria. In some embodiments, each medical policy and clinical guidelines based AI model may be designed using iterative sessions with physicians and other medical practitioners to review model outputs and capture essential feedback. In some embodiments, medical practitioners may determine authorization approvals based on medical necessity criteria. In some embodiments, the trained AI models achieve 96% algorithm decision accuracy as compared to manual review of the same medical record for the same medical necessity question. This accuracy level may be achieved by physicians reviewing the updated version of the model outputs, audit results and signs off on model performance. In some embodiments, explanation outputs may be created (113) to drive decision justification visibility.

For example, the clinical documentation identifies cavernous sinus thrombosis caused chronic sinusitis. In an exemplary method, clinical documentation received from a provider identifies chronic sinusitis greater than 12 weeks duration that interferes with a patient's lifestyle. Member claim history is queried 111 for relevant diagnoses and procedures per medical necessity criteria. For example, for the patient in the past 12 months, 4 claims with chronic sinusitis are identified as submitted.

If the AI model has analyzed the extracted text and member claim history for evidence of medical necessity, the system then determines (114) if medical necessity is met. In some embodiments, this means that the system determines whether the decision tree logic is met, so that at least one required logical subset of necessity criteria groups is met. Automatic authorization is provided (115) for the authorization request if at least one required subset of medical criteria are found (114) in the clinical documentation and/or the patient claim history. In some embodiments, if sufficient medical criteria are not found, which may include a finding that partial medical criteria are present, the case is pended (116) for manual review.

Figure 2A:
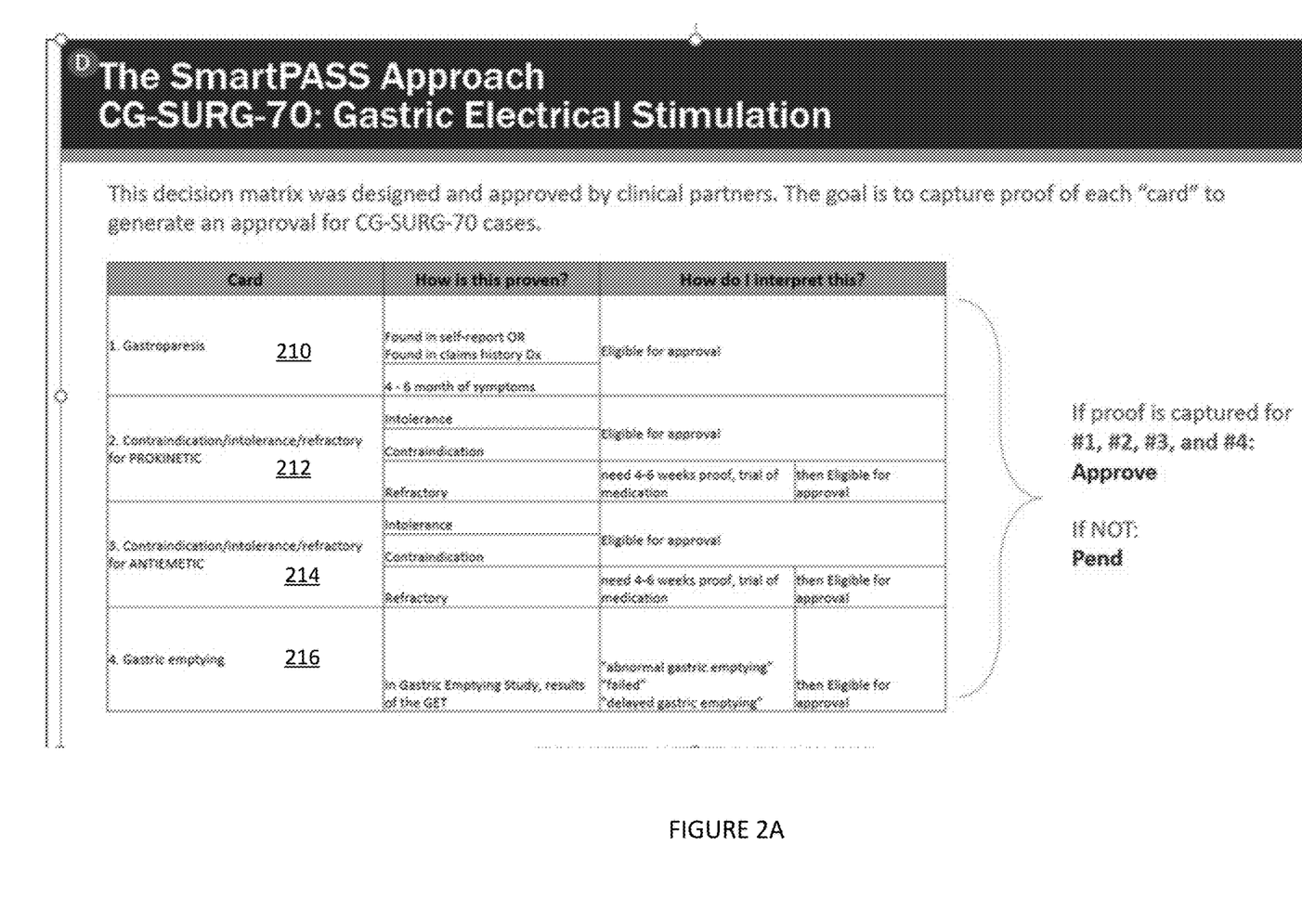
FIG. 2A is a graphical representation of a decision matrix, according to some implementations.
Figure 2B:
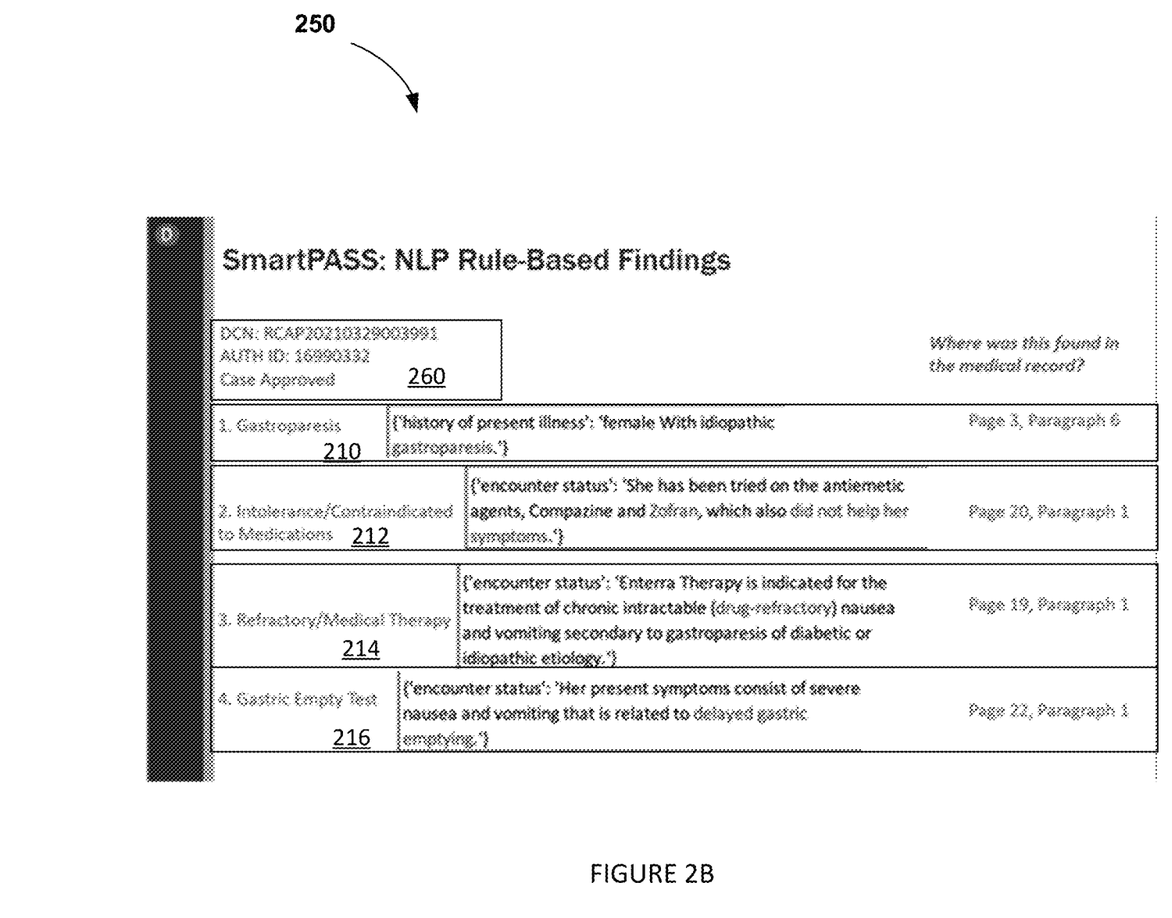
FIG. 2B is a graphical representation of the results of applying natural language processing, according to some implementations.

FIG. 2A is an exemplary necessity concept group decision matrix for identifying proof of the presence in a medical record of four "clinical cards," according to some implementations. As described previously, medical necessity data can be translated into separate necessity concepts, which may be represented in the system by "clinical cards." For example, the trained AI model can be a policy-specific medical necessity rules based model that translates medical necessity data into separate clinical cards, such that some logistical subset of clinical cards is necessary for a finding of medical necessity. As an initial example, for a first case involving gastric electrical stimulation, medical necessity data may be translated into four clinical cards: gastroparesis 210, contraindication for PROKINETIC 212, contraindication for ANTIEMETIC 214 and gastric emptying 216. Each clinical card can be modified based on several modifiers. For example, clinical card gastroparesis 210 represents a medical condition which may have condition modifiers to represent "acuity" (chronic), "change" (exacerbation, worsening, unchanged, no improvement), or "severity" (severe, intractable).

Each clinical card (e.g., gastroparesis 210) can require proof of clinical card identification in the clinical documentation. For example, proof of clinical card identification in the clinical documentation provides validity of the clinical card. For example, for gastroparesis 210, proof of identification in the clinical documentation may include (i) identifying the term "gastroparesis" in the self-report or in the claims history documentation and/or it may include (ii) identifying "gastroparesis" in 4-6 months of symptoms. If either of the conditions are met, the case can be eligible for auto-approval. In some embodiments, upon proof in the self-report that clinical card gastroparesis 210 exists, the case can be eligible for approval. An example of gastroparesis 210 existing in the clinical documentation is provided in Figure B and will be described in more detail in relation to FIG. 2B.

As another example, another clinical card can be contraindication/intolerance/refractory for PROKINETIC 212. Proving clinical card for contraindication/intolerance/refractory for PROKINETIC 212 exists may include identifying "intolerance" or "contraindication". If proof of intolerance or contraindication is present, the case can be eligible for approval. However, if proof of refractory is present, the case may require 4-6 weeks trial of medication in order to then re-try for automatic approval.

As another example, clinical card for contraindication, intolerance, refractory for ANTIEMETIC 214 may require proof of intolerance or a contraindication. If refractory proof is present for clinical card 214, 4-6 weeks trial of medication may be required before auto approval eligibility.

Another example of a clinical card is gastric emptying 216. Proof of the clinical card can require gastric emptying study in the clinical documentation. For example, the following identified text in the clinical documentation can help identify the results: "abnormal gastric emptying", "failed", "delayed gastric emptying, etc.

FIG. 2B is an exemplary user interface illustrating identification of clinical cards described in FIG. 2A, according to some implementations. For example, four clinical cards gastroparesis 210, contraindication for PROKINETIC 212, contraindication for ANTIEMETIC 214 and gastric emptying 216 are searched for in a first case. Since all four clinical cards are found in the clinical record 250 the case is signaled as approved in case status indicator 260. Proof of gastroparesis 210 as shown in FIG. 2A, can be found in the self-report itself. As shown in FIG. 2B, proof of gastroparesis is found on page 3, paragraph 6 by identifying the term "gastroparesis".

As another example, proof of clinical card for intolerance or contraindication to medication 212 can be found in the medical record as "Zofran did not help her", which is identified in page 20, paragraph 1.

As another example, proof of clinical card refractory and medical therapy 214 can be found in page 19, paragraph 1 as "drug-refractory".

Proof of gastric emptying test 216 can be found in page 22, paragraph 1 as: "delayed gastric emptying".

Figure 3:
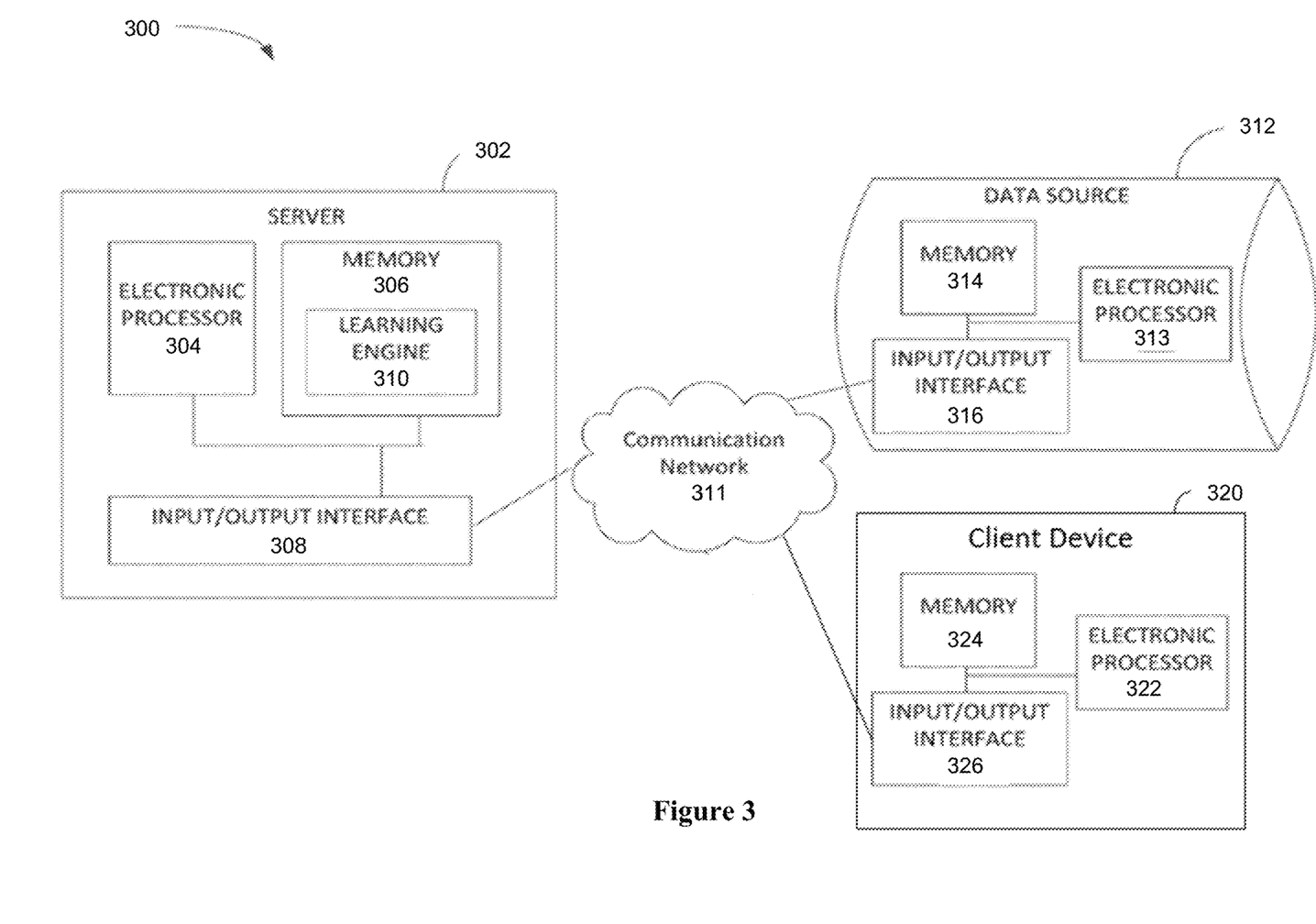
FIG. 3 is a block diagram of a system in accordance with one aspect of the present disclosure.

The foregoing described systems and methods may be implemented via a computer based system such as, for example, the system shown in FIG. 3. FIG. 3 illustrates a system 300 for creating, running, and serving a platform for analysis and display of medical records enhanced by artificial intelligence, according to some embodiments of the invention. The system 300 includes a server 302 that includes a plurality of electrical and electronic components that provide power, operational control, and protection of the components within the server 302. For example, as illustrated in FIG. 3, the server 302 may include an electronic processor 304 (e.g., a microprocessor, application-specific integrated circuit (ASIC), or another suitable electronic device), a memory 306 (e.g., a non-transitory, computer-readable storage medium), and an input/output interface 308. The electronic processor 304, the memory 306, and the input/output interface 308 communicate over one or more connections or buses. The server 302 illustrated in FIG. 3 represents one example of a server, and embodiments described herein may include a server with additional, fewer, or different components than the server 302 illustrated in FIG. 3. Also, in some embodiments, the server 302 performs functionality in addition to the functionality described herein. Similarly, the functionality performed by the server 302 (i.e., through execution of instructions by the electronic processor 304) may be distributed among multiple servers. Accordingly, functionality described herein as being performed by the electronic processor 304 may be performed by one or more electronic processors included in the server 302, external to the server 302, or a combination thereof.

The memory 306 may include read-only memory ("ROM"), random access memory ("RAM") (e.g., dynamic RAM ("DRAM"), synchronous DRAM ("SDRAM"), and the like), electrically erasable programmable read-only memory ("EEPROM"), flash memory, a hard disk, a secure digital ("SD") card, other suitable memory devices, or a combination thereof, which may include transitory memory, non-transitory memory, or both. The electronic processor 304 executes computer-readable instructions ("software") stored in the memory 306. The software may include firmware, one or more applications, program data, filters, rules, one or more program modules, and other executable instructions. For example, the software may include instructions and associated data for performing the methods described herein. For example, as illustrated in FIG. 3, the memory 306 may store a learning engine (e.g., "software") 310 for performing one or more of the functions described herein, which may include probabilistic matching, deterministic matching, machine learning, artificial intelligence, or the like. However, in other embodiments, the functionality described herein as being performed by the learning engine 310 may be performed through one or more software modules stored in the memory 306 or external memory.

The input/output interface 308 allows the server 302 to communicate with devices external to the server 302. For example, as illustrated in FIG. 3, the server 302 may communicate with one or more data sources 312 through the input/output interface 308. In particular, the input/output interface 308 may include a port for receiving a wired connection to an external device (e.g., a universal serial bus ("USB") cable and the like), a transceiver for establishing a wireless connection to an external device (e.g., over one or more communication networks 311, such as the Internet, a local area network ("LAN"), a wide area network ("WAN"), and the like), or a combination thereof.

In some embodiments, the server 302 also receives input from one or more peripheral devices, such as a keyboard, a pointing device (e.g., a mouse), buttons on a touch screen, a scroll ball, mechanical buttons, and the like through the input/output interface 308. Similarly, in some embodiments, the server 302 provides output to one or more peripheral devices, such as a display device (e.g., a liquid crystal display ("LCD"), a touch screen, and the like), a printer, a speaker, and the like through the input/output interface 308. In some embodiments, output may be provided within a graphical user interface ("GUI") (e.g., generated by the electronic processor 304 executing instructions and data stored in the memory 306 and presented on a touch screen or other display) that enables a user to interact with the server 302. In other embodiments, a user may interact with the server 302 through one or more intermediary devices, such as a personal computing device, e.g., laptop, desktop, tablet, smartphone, smartwatch or other wearable device, smart television, and the like. For example, a user may configure functionality performed by the server 302 as described herein by providing data to an intermediary device that communicates with the server 302. In particular, a user may use a browser application executed by an intermediary device to access a web page that receives input from and provides output to the user for configuring the functionality performed by the server 302.

As illustrated in FIG. 3, the system 300 includes one or more data sources 312. Each data source 312 may include a plurality of electrical and electronic components that provide power, operational control, and protection of the components within the data source 312. In some embodiments, each data source 312 represents a server, a database, a personal computing device, or a combination thereof. For example, as illustrated in FIG. 3, each data source 312 may include an electronic processor 313 (e.g., a microprocessor, ASIC, or other suitable electronic device), a memory 314 (e.g., a non-transitory, computer-readable storage medium), and an input/output interface 316. The data sources 312 illustrated in FIG. 3 represent one example of data sources and embodiments described herein and may include a data source with additional, fewer, or different components than the data sources 312 illustrated in FIG. 3. Also, in some embodiments, the server 302 communicates with more or fewer data sources 312 than illustrated in FIG. 3.

The input/output interface 316 allows the data source 312 to communicate with external devices, such as the server 302. For example, as illustrated in FIG. 3, the input/output interface 316 may include a transceiver for establishing a wireless connection to the server 302 or other devices through the communication network 311 described above. Alternatively or in addition, the input/output interface 316 may include a port for receiving a wired connection to the server 302 or other devices. Furthermore, in some embodiments, the data sources 312 also communicate with one or more peripheral devices through the input/output interface 316 for receiving input from a user, providing output to a user, or a combination thereof. In other embodiments, one or more of the data sources 312 may communicate with the server 302 through one or more intermediary devices. Also, in some embodiments, one or more of the data sources 312 may be included in the server 302.

The memory 314 of each data source 312 may store patient data, such as medical records, and the like. For example, the data sources 312 may include an electronic medical record ("EMR") database, a claims database, a patient database, and the like. In some embodiments, as noted above, data stored in the data sources 312 or a portion thereof may be stored locally on the server 302 (e.g., in the memory 306).

User device 320 may also be connected to communication network 311, for communication with server 302 and/or with data source 312. Inputs and outputs 318 may flow between server 302, e.g., via input/output interface 308, and user device 320, e.g., via input/output interface 326. Inputs may include medical records data as described herein, including diagnosis data, medical images, patient biographical data, historical timeline data, and the like. Outputs may include match determinations via probabilistic matching, deterministic matching, and/or machine learning, as described in more detail below.

The foregoing description, for purpose of explanation, has been described with reference to specific implementations. However, the illustrative discussions above are not intended to be exhaustive or to limit the scope of the claims to the precise forms disclosed. Many modifications and variations are possible in view of the above teachings. The implementations are chosen in order to best explain the principles underlying the claims and their practical applications, to thereby enable others skilled in the art to best use the implementations with various modifications as are suited to the particular uses contemplated.

What is claimed is:

1. A machine learning based method for authorizing the performance of a treatment, comprising the steps of:
   receiving a treatment authorization request for a treatment, the treatment authorization request including a historical record of the person who will receive the treatment and treatment identifying information relating to the treatment;
   creating an extracted text of the historical record using optical character recognition on the historical record;
   determining whether to analyze authorization performance of the treatment using a machine learning authorization process, wherein the determination is based on treatment identifying information and whether treatment authorization guidelines exist for the treatment;
   in response to a determination to analyze authorization performance of the treatment using a machine learning authorization process:
      identifying authorization criteria for the treatment based on the treatment authorization guidelines, wherein the authorization criteria includes records data conditional to authorization of performance of the treatment;
      identifying a natural language record processing model corresponding to the treatment authorization guidelines;
      performing natural language processing on the extracted text of the record in accordance with the identified natural language record processing model to identify relevant record data in the record;
      determining whether the relevant record data meets the authorization criteria;

in response to a determination that the relevant record data meets the authorization criteria, authorizing the treatment; and in response to a determination that the relevant record data does not meet the authorization criteria:

recognizing a specified keyword within the extracted text, using a named entity recognition model (NER), wherein the NER is trained using policy data relating to a policy having the policy type, and wherein the specified keyword is identified as relating to the policy type; and displaying a visual representation of the clinical document on a display, wherein the visual representation comprises a visual indicator of the presence of the specified keyword on the page.

2. The method of claim 1, further comprising cropping and deskewing each page of the historical record prior to the step of creating the extracted text.

3. The method of claim 1, wherein the authorization criteria comprise a plurality of necessity concept groups, wherein each of the plurality of necessity concept groups comprises a plurality of words of phrases corresponding to one authorization criterion.

4. The method of claim 3, further comprising:
creating a decision tree comprising Boolean logical operators applied to the plurality of necessity concept groups to create at least one subset of necessity concept groups that are required to be found in the historical record and
traversing the decision tree to determine whether the relevant record data meets the authorization criteria.

5. The method of claim 1, wherein the treatment is a medical treatment and wherein the historical record is a medical record.

6. The method of claim 5, wherein the treatment authorization guidelines relate to a medical necessity of the medical treatment.

7. The method of claim 6, further comprising the steps of, in response to a determination that the relevant record data does not meet the authorization criteria:
analyzing the extracted text to generate the classification label for each page of the medical record, using a multinomial classifier model comprising a long short-term memory (LSTM) neural network, wherein the multinomial classifier model has been trained to recognize different classes of pages, based on similarities to a corpus of historical pages that have been previously classified; and
displaying the visual representation of the clinical document on the display, wherein the visual representation further comprises a visual indicator of the classification label.

8. A system comprising:
one or more memory units each operable to store at least one program; and
at least one processor communicatively coupled to the one or more memory units, in which the at least one program, when executed by the at least one processor, causes the at least one processor to perform the steps of:
receiving a treatment authorization request for a treatment, the treatment authorization request including a historical record of the person who will receive the treatment and treatment identifying information relating to the treatment;
creating an extracted text of the historical record using optical character recognition on the historical record;
determining whether to analyze authorization performance of the treatment using a machine learning authorization process, wherein the determination is based on treatment identifying information and whether treatment authorization guidelines exist for the treatment;
in response to a determination to analyze authorization performance of the treatment using a machine learning authorization process:
identifying authorization criteria for the treatment based on the treatment authorization guidelines, wherein the authorization criteria includes records data conditional to authorization of performance of the treatment;
identifying a natural language record processing model corresponding to the treatment authorization guidelines;
performing natural language processing on the extracted text of the record in accordance with the identified natural language record processing model to identify relevant record data in the record;
determining whether the relevant record data meets the authorization criteria; and
in response to a determination that the relevant record data meets the authorization criteria, authorizing the treatment; and
in response to a determination that the relevant record data does not meet the authorization criteria:
recognizing a specified keyword within the extracted text, using a named entity recognition model (NER), wherein the NER is trained using policy data relating to a policy having the policy type, and wherein the specified keyword is identified as relating to the policy type; and
displaying a visual representation of the clinical document on a display, wherein the visual representation comprises a visual indicator of the presence of the specified keyword on the page.

9. A non-transitory computer readable storage medium having stored thereon computer-executable instructions which, when executed by a processor, perform the steps of:
receiving a treatment authorization request for a treatment, the treatment authorization request including a historical record of the person who will receive the treatment and treatment identifying information relating to the treatment;
creating an extracted text of the historical record using optical character recognition on the historical record;
determining whether to analyze authorization performance of the treatment using a machine learning authorization process, wherein the determination is based on treatment identifying information and whether treatment authorization guidelines exist for the treatment;
in response to a determination to analyze authorization performance of the treatment using a machine learning authorization process:
identifying authorization criteria for the treatment based on the treatment authorization guidelines, wherein the authorization criteria includes records data conditional to authorization of performance of the treatment;
identifying a natural language record processing model corresponding to the treatment authorization guidelines;
performing natural language processing on the extracted text of the record in accordance with the identified natural language record processing model to identify relevant record data in the record;

determining whether the relevant record data meets the authorization criteria; and in response to a determination that the relevant record data meets the authorization criteria, authorizing the treatment; and in response to a determination that the relevant record data does not meet the authorization criteria:
  recognizing a specified keyword within the extracted text, using a named entity recognition model (NER), wherein the NER is trained using policy data relating to a policy having the policy type, and wherein the specified keyword is identified as relating to the policy type; and
  displaying a visual representation of the clinical document on a display, wherein the visual representation comprises a visual indicator of the presence of the specified keyword on the page.

* * * * *